(12) United States Patent
Fernandez

(10) Patent No.: US 8,098,794 B1
(45) Date of Patent: Jan. 17, 2012

(54) MOVING-ARTICLE X-RAY IMAGING SYSTEM AND METHOD FOR 3-D IMAGE GENERATION

(75) Inventor: Kenneth R. Fernandez, Hampton Cove, AL (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 112 days.

(21) Appl. No.: 12/558,319

(22) Filed: Sep. 11, 2009

(51) Int. Cl.
*G01N 23/083* (2006.01)
*H05G 1/62* (2006.01)
(52) U.S. Cl. .......... 378/57; 378/62; 378/98.12
(58) Field of Classification Search ........... 378/4–20, 378/51, 57, 62, 92, 98.12, 210
See application file for complete search history.

(56) References Cited

U.S. PATENT DOCUMENTS

| | | | | |
|---|---|---|---|---|
| 5,524,133 A * | 6/1996 | Neale et al. | | 378/53 |
| 5,541,856 A * | 7/1996 | Hammermeister | | 378/196 |
| 6,163,591 A | 12/2000 | Benjamin | | |
| 6,195,205 B1 | 2/2001 | Faris | | |
| 6,473,487 B1 | 10/2002 | Le | | |
| 6,661,867 B2 | 12/2003 | Mario et al. | | |
| 6,904,122 B2 | 6/2005 | Swift et al. | | |
| 6,928,131 B2 | 8/2005 | Olshansky et al. | | |
| 6,968,034 B2 | 11/2005 | Ellengogen | | |
| 6,973,161 B2 | 12/2005 | Ohtsuki | | |
| 7,012,987 B1 | 3/2006 | Annis | | |
| 7,319,737 B2 * | 1/2008 | Singh | | 378/57 |
| 7,362,847 B2 * | 4/2008 | Bijjani | | 378/57 |
| 7,505,554 B2 * | 3/2009 | Ting | | 378/19 |
| 7,656,995 B2 * | 2/2010 | Robinson | | 378/41 |
| 2005/0025280 A1 * | 2/2005 | Schulte | | 378/57 |
| 2005/0220265 A1 | 10/2005 | Besson | | |
| 2006/0078085 A1 * | 4/2006 | Zanker | | 378/57 |
| 2007/0237293 A1 * | 10/2007 | Singh | | 378/57 |

* cited by examiner

*Primary Examiner* — Anastasia Midkiff
(74) *Attorney, Agent, or Firm* — Peter J. Van Bergen; James J. McGroary

(57) ABSTRACT

An x-ray imaging system and method for a moving article are provided for an article moved along a linear direction of travel while the article is exposed to non-overlapping x-ray beams. A plurality of parallel linear sensor arrays are disposed in the x-ray beams after they pass through the article. More specifically, a first half of the plurality are disposed in a first of the x-ray beams while a second half of the plurality are disposed in a second of the x-ray beams. Each of the parallel linear sensor arrays is oriented perpendicular to the linear direction of travel. Each of the parallel linear sensor arrays in the first half is matched to a corresponding one of the parallel linear sensor arrays in the second half in terms of an angular position in the first of the x-ray beams and the second of the x-ray beams, respectively.

9 Claims, 3 Drawing Sheets

MOVING-ARTICLE X-RAY IMAGING SYSTEM AND METHOD FOR 3-D IMAGE GENERATION

ORIGIN OF THE INVENTION

The invention was made by an employee of the United States Government and may be manufactured and used by or for the Government for governmental purposes without the payment of any royalties.

BACKGROUND OF THE INVENTION

1. Field of the Invention

This invention relates to x-ray imaging systems and methods. More specifically, the invention is an x-ray imaging system and method for use in generating three-dimensional images of moving articles on a conveyor.

2. Description of the Related Art

X-ray imagining of moving articles is used extensively for luggage/package screening at security check points, as well as industrial applications to include the monitoring of parts/assemblies moving along an assembly line. Most x-ray imagining systems used by commercial or government entities for these purposes generate two-dimensional images of a moving article.

More recently, U.S. Pat. No. 6,763,083 disclosed an article screening system that generated two sets of x-ray images from two slightly different perspectives. The two sets of images are made at different sensor positions along a conveyor as an article being screened is transported on the conveyor past each of two x-ray image sensors. Each sensor's center-of-view is combined with data from a position attached to the conveyor. Conveyor position data is read continuously and is stored with the two sets of images so that appropriate "left eye" and "right eye" image set can be presented simultaneously on a commercially-available three-dimensional display. Typically, a human inspector viewing the three-dimensional display must wear special glasses to view the image in three dimensions. While this patented system provides more information than the conventional two-dimension x-ray imaging system, the three-dimensional image presented by the '083 system is limited to the "center-of-view" view point of the two "left" and "right x-ray image sensor positions. This leads to inspection delays and inaccuracies as an inspector often must perform multiple reviews in an effort to discern objects in the presented image.

SUMMARY OF THE INVENTION

Accordingly, it is an object of the present invention to provide a system and method that can be used to generate a three-dimensional image of a moving article.

Another object of the present invention is to provide an x-ray imaging system and method that can be used to generate a three-dimensional image of a moving article that provides multiple perspectives of the article.

Other objects and advantages of the present invention will become more obvious hereinafter in the specification and drawings.

In accordance with the present invention, an x-ray imaging system and method for a moving article are provided. The article is moved along a linear direction of travel while the article is exposed to non-overlapping x-ray beams such that each non-overlapping x-ray beam passes through the article. A plurality of parallel linear sensor arrays are disposed in the x-ray beams after they pass through the article. More specifically, a first half of the plurality are disposed in a first of the x-ray beams passed through the article while a second half of the plurality are disposed in a second of the x-ray beams passed through the article. Each of the parallel linear sensor arrays is oriented perpendicular to the linear direction of travel. Each of the parallel linear sensor arrays generates a linear x-ray image of the article. Each of the parallel linear sensor arrays in the first half is matched to a corresponding one of the parallel linear sensor arrays in the second half in terms of an angular position in the first of the x-ray beams and the second of the x-ray beams, respectively.

BRIEF DESCRIPTION OF THE DRAWING(S)

Other objects, features and advantages of the present invention will become apparent upon reference to the following description of the preferred embodiments and to the drawings, wherein corresponding reference characters indicate corresponding parts throughout the several views of the drawings and wherein.

DESCRIPTION OF THE PREFERRED EMBODIMENT(S)

Figure 1:
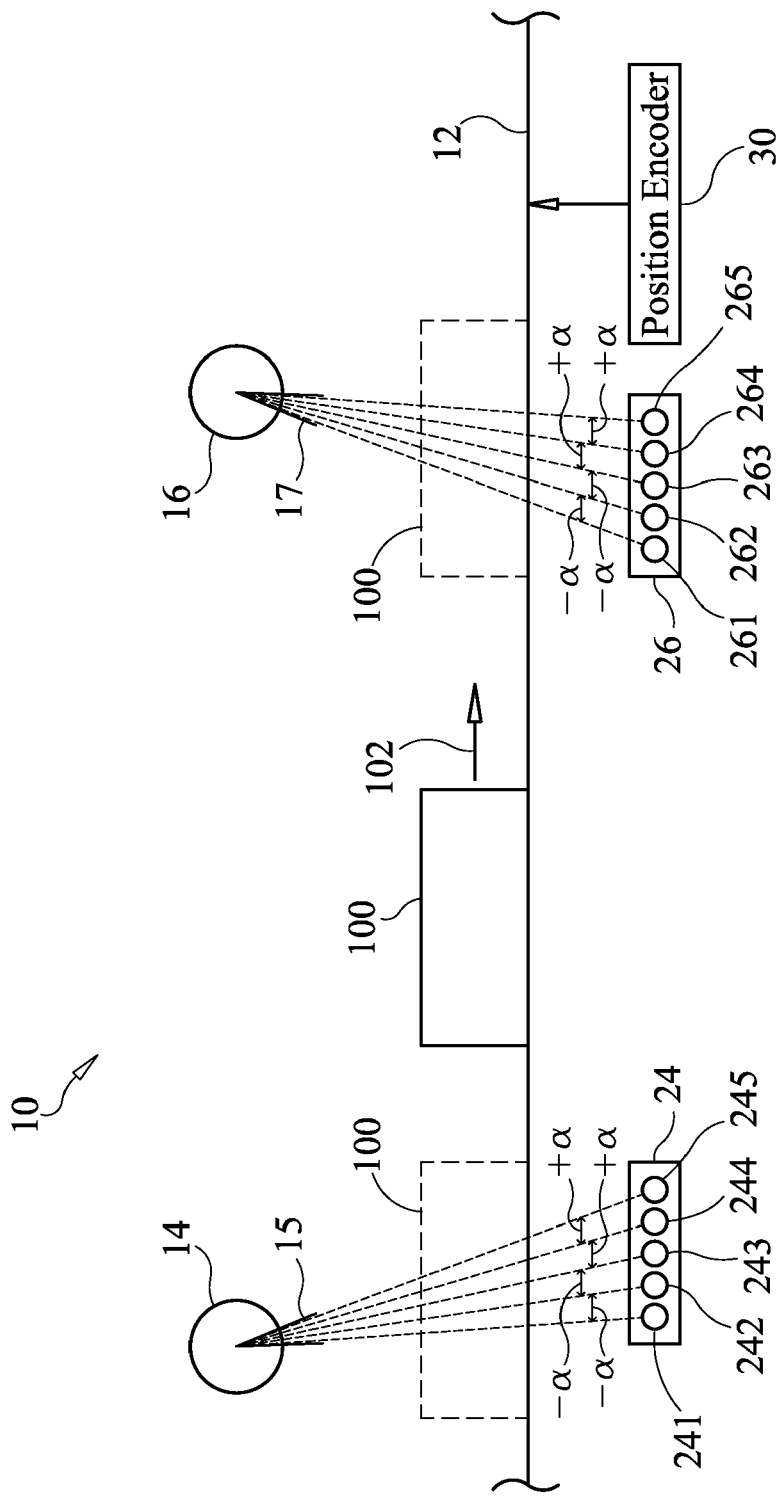
FIG. 1 is a schematic view of a moving-article x-ray imaging system in accordance with an embodiment of the present invention.

Referring now to the drawings and more particularly to FIG. 1, a schematic view of a moving article x-ray imaging system in accordance with an embodiment of the present invention is shown and is referenced generally by numeral 100 where the left and right dashed-line images of article 100 represent the article's past and future positions, respectively, as article 100 moves along a linear direction of travel from left to right as indicated by arrow 102. The application environment for system 10 is not a limitation of the present invention as article 100 could be luggage or a package being screened for security purposes, a part being examined for defects or verification, an assembly being examined for adherence to safety or fabrication specifications, etc. By way of example, system 10 will be described for use in an x-ray luggage/package screening application where article 100 is a piece of luggage placed on a moving conveyor 12 that is assumed to be moving article 100 along linear direction of travel 102.

System 10 includes two x-ray sources 14 and 16 positioned such that their respective generated x-ray beams 15 and 17 are directed towards the traversed path of article 100 from the same side thereof, e.g., from above conveyor 12 in the illustrated embodiment. As would be understood in the art, each of x-ray beams 15 and 17 fans out as illustrated such that a portion (or all) of article 100 is disposed in beam 15 and then in beam 17 as article 100 moves on conveyor 12. That is, beams 15 and 17 are non-overlapping x-ray beams from the perspective of article 100 moving along linear direction of travel 102.

In accordance with the present invention, x-ray sensor arrangements 24 and 26 are placed in respective ones of x-ray beams 15 and 17 at locations therein that are after beams 15 and 17 have passed through article 100 as it moves along conveyor 12. In general, each of sensor arrangements 24 and 26 senses x-ray information in respective beams 15 and 17 from multiple viewpoints or perspectives therein. More specifically, each of sensor arrangements 24 and 26 sense multiple scan lines of x-ray information in respective x-ray beams 15 and 17. Each scan line is perpendicular to linear direction of travel 102 such that all scan lines are parallel to one another. Furthermore, the number of scan lines is the same in each of sensor arrangements 24 and 26 with each scan line in sensor arrangement 24 having a corresponding scan line in sensor arrangement 26. Such corresponding scan lines are matched in terms of their angular orientation in x-ray beams 15 and 17.

Figure 2:
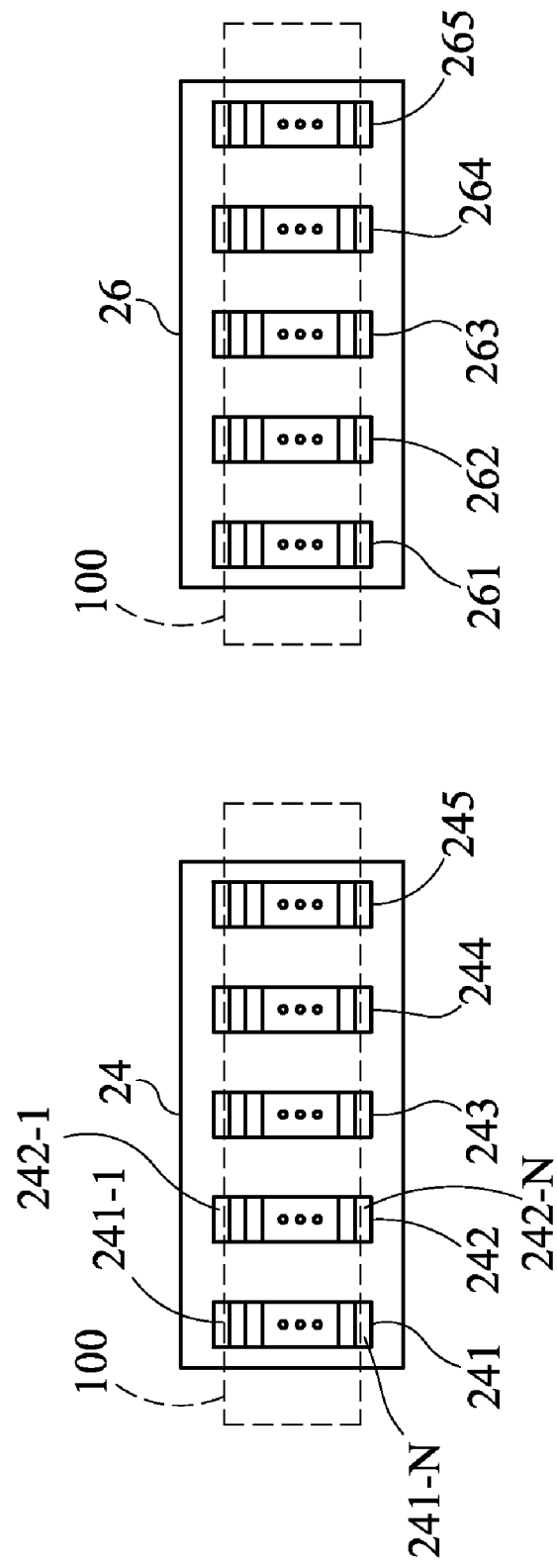
FIG. 2 is a schematic plan view of two x-ray sensor arrangements used in an embodiment of the present invention.

By way of example, one embodiment of sensor arrangements 24 and 26 will be explained with continued reference to FIG. 1 and additional reference to FIG. 2. Since the sensor arrangements are essentially identical in form and function, only sensor arrangement 24 will be described in detail herein. In the illustrated embodiment, sensor arrangement 24 has five linear sensor arrays 241-245 that are parallel to one another and perpendicular to linear direction of travel 102. However, it is to be understood that more or fewer parallel linear sensor arrays could be used, and that the number thereof in each sensor arrangement could be even or odd without departing from the scope of the present invention. Each of sensor arrays 241-245 is located at a unique angular orientation of x-ray beam 15. Sensor array 241 has linearly aligned sensors 241-1, ..., 241-N; sensor array 242 has linearly aligned sensors 242-1, ..., 242-N, etc. Sensor array 243 is typically located centrally in x-ray beam 15 with sensor arrays 242 and 244 spaced apart from array 243 at angular orientations of, for example, $-\alpha$ and $+\alpha$ relative to the angular orientation of sensor array 243. Sensor arrays 241 and 245 are spaced respectively apart from arrays 242 and 244 at angular orientations of, for example, $-\alpha$ and $+\alpha$ relative to the angular orientations of sensor array 242 and 244. That is, sensor arrays 241-245 are uniformly spaced in terms of their angular orientation in x-ray beam 15. However, it is to be understood that the angular spacing between sensor arrays 241-245 could also be non-uniform without departing from the scope of the present invention.

While spacing between the linear sensor arrays in each of arrangements 24 and 26 can be uniform or non-uniform, there must be a relative one-to-one correspondence between the two sensor arrangements with one linear sensor array forming the basis for the relative correspondence. For example, in the illustrated example, sensor array 243 could be considered the basis for relative correspondence. Accordingly, sensor array 243 is matched with sensor array 263 to form a pair of scan lines of x-ray image data. For matching purposes in the present invention, sensor array 262 is angularly spaced relative to sensor array 263 by $-\alpha$ while sensor array 264 is angularly spaced relative to sensor array 263 by $+\alpha$. Thus, sensor arrays 242 and 262 are said to be matched to form another pair of scan lines of x-ray image data with this pair offering a different angular perspective of article 100, while sensor arrays 244 and 264 are matched to form yet another pair of scan lines x-ray image data to offer yet another angular perspective of article 100. The above description is readily extended to sensor array pairs 241/261 and 245/265.

Figure 3:
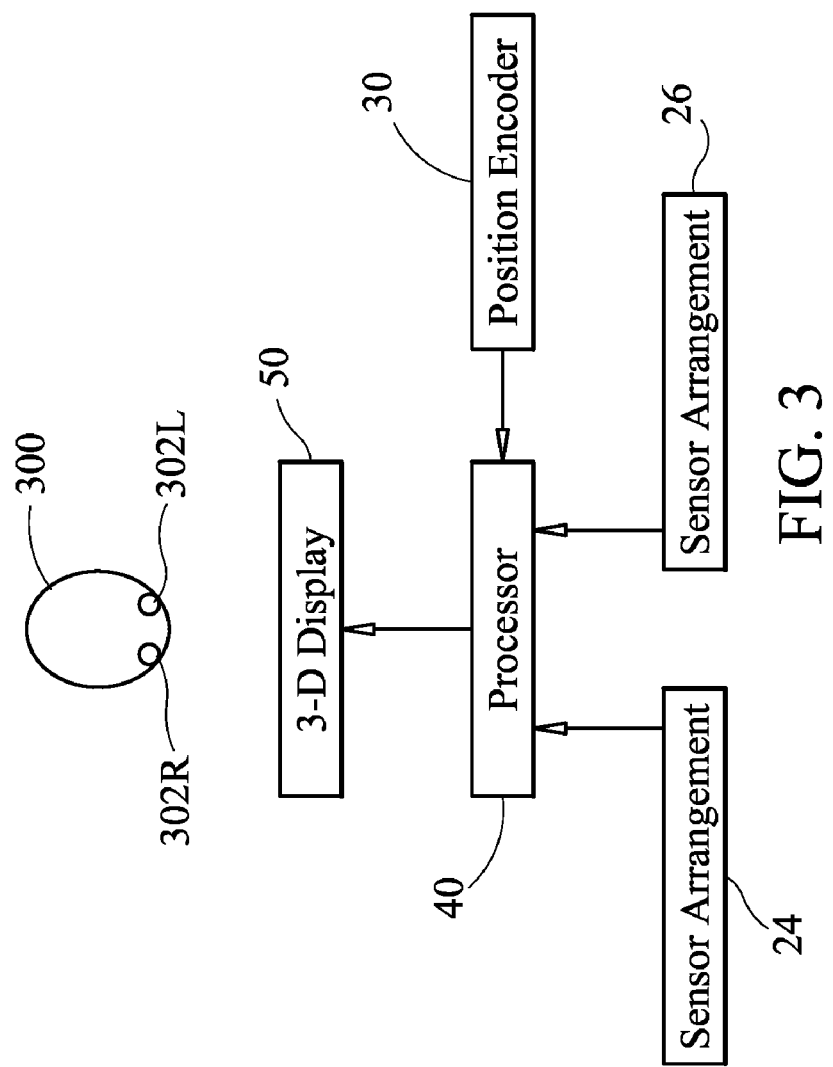
FIG. 3 is a schematic view of a processing and display system for use with the present invention.

In essence, the above-described system 10 generates x-ray images for different vantage points in the x-ray beams. When the x-ray image data is presented to a three-dimensional display device (not shown) that is also provided with position of conveyor 12 (e.g., provided by a position encoder 30), multiple three-dimensional views of article 100 can be generated. In this way, an operator viewing such a display could select/change the view in order to better examine what is inside article 100. Accordingly, and with additional reference to FIG. 3, the x-ray image data sense/collected by sensor arrangements 24 and 26 is provided to a processor 40 along with conveyor position data from encoder 30. For each of the above-described matched sensor array pairs, processor 40 could implement an image merging process such as that disclosed in the afore-mentioned U.S. Pat. No. 6,763,083, the contents of which are hereby incorporated by reference.

The merged image data is provided to a three-dimensional image display 50, the choice of which is not a limitation of the present invention. A human operator 300 having right and left eyes 302R and 302L, respectively, will view display 50. To select a particular "view" sensed/collected by arrangements 24 and 26, several different types of human interfaces could be used without departing from the scope of the present invention. For example, side-to-side head movement of operator 300 could be used to select the viewing angle. Another option is to provide operator 300 with a conventional hand or foot-operated controller (not shown) to select the desired viewing angle. Still further, some three-dimensional displays are equipped with vertically-oriented Fresnel diffraction gratings that provide for alternate views by detecting changes in one's head position.

The advantages of the present invention are numerous. An x-rayed moving article can be viewed from a variety of angular perspectives thereby allowing an operator/viewer to see the inner contents of the article from multiple perspectives. The present invention will have immediate applicability to a variety of commercial and governmental x-ray imaging applications.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. An x-ray imaging system for a moving article, comprising:

a conveyor device for moving an article adapted to be placed thereon along a linear direction of travel;

a first x-ray source for directing a first x-ray beam towards said conveyor device wherein said first x-ray beam passes through the article moving along said conveyor device;

a second x-ray source for directing a second x-ray beam towards said conveyor device wherein said second x-ray beam passes through the article moving along said conveyor device, said first x-ray beam and said second x-ray beam being non-overlapping;

a first sensor arrangement disposed in said first x-ray beam passed through the article moving along said conveyor device, said first sensor arrangement defined by at least two parallel linear sensor arrays oriented perpendicular to said linear direction of travel of said conveyor device and spaced apart from one another along said linear direction of travel;

a second sensor arrangement disposed in said second x-ray beam passed through the article moving along said conveyor device, said second sensor arrangement defined by at least two parallel linear sensor arrays oriented perpendicular to said linear direction of travel of said conveyor device and spaced apart from one another along said linear direction of travel, wherein relative spacing between said arrays associated with said first sensor arrangement is identical to relative spacing between said arrays associated with said second sensor arrangement; and a processor for merging image data collected by each of said arrays associated with said first sensor arrangement with a unique one of said arrays associated with said second sensor arrangement based on one-to-one correspondence between said relative spacing associated with said first sensor arrangement and said second sensor arrangement.

2. An x-ray imaging system as in claim 1, further comprising means for detecting a position of said conveyor device where the article is located.

3. An x-ray imaging system as in claim 1, wherein each of said first sensor arrangement and said second sensor arrangement comprises an odd number of said parallel linear sensor arrays.

4. An x-ray imaging system as in claim 1, further comprising a display system coupled to said processor for displaying a three-dimensional image for each said image data so-merged.

5. An x-ray imaging system for a moving article, comprising:
 a conveyor device for moving an article adapted to be placed thereon along a linear direction of travel;
 a first x-ray source for directing a first x-ray beam towards said conveyor device wherein said first x-ray beam passes through the article moving along said conveyor device;
 a second x-ray source for directing a second x-ray beam towards said conveyor device wherein said second x-ray beam passes through the article moving along said conveyor device, said first x-ray beam and said second x-ray beam being non-overlapping;
 a first sensor arrangement disposed in said first x-ray beam passed through the article moving along said conveyor device, said first sensor arrangement defined by an odd number of at least three parallel linear sensor arrays oriented perpendicular to said linear direction of travel of said conveyor device at unique locations within said first x-ray beam and spaced apart from one another along said linear direction of travel;
 a second sensor arrangement disposed in said second x-ray beam passed through the article moving along said conveyor device, said second sensor arrangement defined by an odd number of at least three parallel linear sensor arrays oriented perpendicular to said linear direction of travel of said conveyor device at unique locations within said second x-ray beam and spaced apart from one another along said linear direction of travel, wherein relative spacing between said arrays associated with said first sensor arrangement is identical to relative spacing between said arrays associated with said second sensor arrangement; and
 a processor for merging image data collected by each of said arrays associated with said first sensor arrangement with a unique one of said arrays associated with said second sensor arrangement based on one-to-one correspondence between said relative spacing associated with said first sensor arrangement and said second sensor arrangement.

6. An x-ray imaging system as in claim 5, further comprising means for detecting a position of said conveyor device where the article is located.

7. An x-ray imaging system as in claim 5, further comprising a display system coupled to said processor for displaying a three-dimensional image for each said image data so-merged.

8. A method of x-ray imaging a moving article, comprising the steps of:
 moving an article along a linear direction of travel;
 exposing the article to non-overlapping x-ray beams while moving along said linear direction of travel, wherein each of said non-overlapping x-ray beams passes through the article;
 generating a linear x-ray image at each of at least four parallel image scan-line locations with a first half thereof disposed in a first of said non-overlapping x-ray beams passed through the article and a second half thereof disposed in a second of said non-overlapping x-ray beams passed through the article, each of said parallel image scan-line locations oriented perpendicular to said linear direction of travel and spaced apart from one another along said linear direction of travel, wherein relative spacing between said parallel image scan-line locations associated with said first half is identical to relative spacing between said parallel image scan-line locations associated with said second half; and
 merging each said linear x-ray image generated at said parallel image scan-line locations associated with said first half with a unique one of said linear x-ray images generated at said parallel image scan-line locations associated with said second half based on one-to-one correspondence between said relative spacing associated with said first half and said second half.

9. A method according to claim 8, wherein said at least four parallel image scan-line locations comprises an even number of said parallel image scan-line locations.

* * * * *